United States Patent
Ruehrnschopf

(10) Patent No.: US 7,462,832 B2
(45) Date of Patent: Dec. 9, 2008

(54) DEVICE AND METHOD FOR COMPUTER TOMOGRAPHY

(75) Inventor: Ernstpeter Ruehrnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 25 days.

(21) Appl. No.: 11/455,249

(22) Filed: Jun. 16, 2006

(65) Prior Publication Data

US 2006/0284099 A1 Dec. 21, 2006

(30) Foreign Application Priority Data

Jun. 17, 2005 (DE) .................. 10 2005 028 225

(51) Int. Cl.
*G01T 1/161* (2006.01)
(52) U.S. Cl. .................. 250/363.07; 250/363.04; 382/131; 378/4; 378/7
(58) Field of Classification Search ............ 250/363.01, 250/363.02, 363.04; 378/4, 21, 7, 98.11, 378/98.12; 382/131
See application file for complete search history.

(56) References Cited

U.S. PATENT DOCUMENTS

| | | | | |
|---|---|---|---|---|
| 4,714,997 | A * | 12/1987 | Crawford et al. ............ | 600/425 |
| 5,666,391 | A | 9/1997 | Ohnesorge et al. | |
| 6,125,193 | A * | 9/2000 | Han ............................ | 382/131 |
| 6,134,297 | A * | 10/2000 | Chao ........................ | 378/98.12 |
| 6,256,367 | B1 * | 7/2001 | Vartanian ................... | 378/7 |
| 6,639,964 | B2 * | 10/2003 | Schneider et al. ............ | 378/7 |
| 6,721,387 | B1 * | 4/2004 | Naidu et al. ................ | 378/8 |
| 6,879,715 | B2 * | 4/2005 | Edic et al. ................... | 382/132 |
| 2002/0097830 | A1 | 7/2002 | Raupach | |
| 2006/0067461 | A1 * | 3/2006 | Yin et al. ..................... | 378/5 |
| 2006/0109949 | A1 * | 5/2006 | Tkaczyk et al. ............. | 378/4 |
| 2006/0159223 | A1 * | 7/2006 | Wu et al. ..................... | 378/18 |

FOREIGN PATENT DOCUMENTS

| | | |
|---|---|---|
| DE | 195 23 090 C1 | 8/1996 |
| DE | 100 51 462 A1 | 4/2002 |
| DE | 103 20 233 A1 | 12/2004 |

OTHER PUBLICATIONS

Feldkamp et al., "Practical cone-beam algorithm", J.Opt.Soc.Am.A, 1984, p. 612-619, vol. 1, No. 6.
Hsieh et al., "An iterative approach to the beam hardening correction in cone beam CT" Medical Physics, Jan. 2000, p. 23-29, vol. 27, No. 1.
Ohnesorge et al., "Efficient Object Scatter Correction Algorithm for Third and Fourth Generation CT Scanners", European Radiology. 9(3), 1999, p. 563-569.

(Continued)

*Primary Examiner*—David P Porta
*Assistant Examiner*—Casey Bryant

(57) ABSTRACT

A device and a method for computer tomography are described, in which an uncorrected volume image and a correction volume image are overlaid by the user after selection of a weighting function. This enables manual correction to be undertaken even after the correction of interference effects, such as x-ray scattering or beam hardening.

14 Claims, 4 Drawing Sheets

OTHER PUBLICATIONS

Joseph et al., "A Method for Correcting Bone Induced Artifacts in Computed Tomography Scanners", Journal of Computer Assisted Tomography, Jan. 1978, p. 100-108, vol. 2.

Alexander Katsevich, "Analysis of an Exact Inversion Algorithm for Spiral Cone-Beam CT", Phys. Med. Biol. vol. 47, Aug. 2002, pp. 2583-2597, Abstract.

K. Wiesent, K. Barth, N. Navab, P. Durlak, T. Brunner, O. Schuetz and W. Sissler, "Enhanced 3-D-reconstruction algorithm for C-arm systems suitable for inteventional procedures", Medical Imaging, IEEE Trans., May 2000, vol. 19, Issue 5, pp. 391-403, Abstract.

\* cited by examiner

DEVICE AND METHOD FOR COMPUTER TOMOGRAPHY

CROSS REFERENCE TO RELATED APPLICATIONS

This application claims priority of German application No. 10 2005 028 225.3 filed Jun. 17, 2005, which is incorporated by reference herein in its entirety.

FIELD OF THE INVENTION

The invention relates to a device for computer tomography with:
- a radiographic source illuminating an object to be examined from a variety of projection directions;
- a detector recording the radiation from the radiographic source and
- an evaluation unit connected downstream from the detector which reconstructs from the projection images a volume image of the object to be investigated and corrects the image errors in the volume image caused by interference effects.

The invention further relates to a method for reconstruction of volume images from projection images of an object to be investigated.

BACKGROUND OF THE INVENTION

Such a device and such a method are known from DE 100 51 462 A1. The known device comprises an x-ray source and an x-ray detector, which together move around an object to be investigated. The projection images recorded by the x-ray detector are routed to an image processor which corrects the beam hardening. In this case the image processor executes a post-reconstructive correction process. Within the framework of the post-reconstructive process, the image processor reconstructs volume images from the object to be investigated. The term volume images used here and below should be taken to be both three-dimensional and also two-dimensional cross-sectional images. A re-projection is then performed with only those pixels for which the image value lies above a predetermined threshold being taken into account. This enables the processing effort involved in re-projection to be reduced.

Furthermore a method and a device are known from DE 195 23 090 C1 which are used to correct image errors caused by x-ray scattering. With the known device and the known method scatter distribution is modeled on the basis of a physical model for the x-ray scatter and with the aid of the model for the x-ray scattering x-ray scatter amounts falling on the individual pixels of the detector are determined. The x-ray scatter amounts thus determined are then subtracted from the image values of the uncorrected projection images.

Both the beam hardening and also the x-ray scattering are non-linear effects which result in distortion of the reconstructed volume images when the volume images are reconstructed from the projection images. These image artifacts are especially striking in the form of bar artifacts or shadow artifacts in the soft tissue between heavily absorbent bone structures. These image artifacts can significantly adversely affect the quantitative accuracy of the volume images and lead to incorrect diagnoses.

The introduction of computer tomography devices with multi-line detectors and flat-panel detectors has meant that x-ray scatter correction through suitable image processing has become increasingly important. This is because suppression of x-ray scatter by masking it out is very expensive. Correcting these interference effects by suitable image processing is also expensive however. To restrict the processing effort involved in correcting x-ray scatter, simplified scatter models are usually employed, but such models are prone to systematic errors. The image errors caused by x-ray scatter in the reconstructed volume images can thus mostly not be entirely eliminated.

The situation is similar with the correction of beam hardening. It is possible with a known chemical composition of the object to be investigated to perform a precise correction of the hardening. However as a rule the precise chemical composition of the object to be investigated, especially the chemical composition of the bones in the human body is not known in detail. Thus, even after the correction of beam hardening certain shadow artifacts are left behind. A typical example of such effects known to the person skilled in the art is shadow effects between the petrous bones in the anterior cranial fossa.

A further source of errors can be an incorrect scaling of the projection images. Because of the linearity of the reconstruction of the volume image from the projection data it is not necessary as a rule to correctly scale the projection data beforehand, since the volume image can still also be re-scaled after the reconstruction. However this no longer applies if non-linear effects such as spectral hardening or x-ray scattering and their corrections are taken into account in the creation of the volume image. Thus an incorrect scaling of the projection images of for example 10% can lead to an error of significantly more than 10% in the x-ray scatter correction.

SUMMARY OF THE INVENTION

Using this prior art as its starting point, the object of the invention is to create a device and a method with improved options for correction of image errors.

These objects are achieved by a device and a method with the features of the independent claims. Advantageous embodiments and developments are specified in their dependent claims.

In the correction of image errors the projection images recorded by the detector are usually corrected first. As a rule a correction projection image is created for them in each case. Because of the linearity of the reconstruction method used for the reconstruction, a reconstruction which is based on the combination of the projection images with the correction projection images leads to a corrected volume image which corresponds to the combination of an uncorrected volume image based on the uncorrected projection images with a correction volume image based on the correction projection image. Thus it is basically possible to create an uncorrected volume image and a correction volume image in each case which can be overlaid after the conclusion of the reconstruction. If the overlaying is undertaken with the aid of a weighting function selectable by a user, the user can employ his empirical knowledge in the correction of the volume images or if necessary through repeated attempts select an appropriate combination of uncorrected volume image and correction and volume image for the application involved.

With a preferred embodiment the evaluation unit uses a reconstruction algorithm to approximately create from projection images an object model of the object to be investigated and with the aid of a re-projection creates from the object model corrected projection images from which the evaluation unit creates the correction volume image, so that an object-specific correction of the image errors can be undertaken.

In a further embodiment the image values of uncorrected volume image and correction volume image are combined in a linear manner. This embodiment is particularly suitable because of its simplicity if the suitable combination of the uncorrected volume image and correction volume image is to be determined in a number of attempts.

In addition it is possible to undertake a non-linear combination of uncorrected volume image and correction volume image by the evaluation unit using a weighting function of which the arguments are the image values of the correction image. This makes it possible to adapt the image value distribution of the correction volume image to the image value distribution of the uncorrected volume image.

Furthermore it is possible to weight the correction image with a spatial window function and to superimpose a locally-restricted correction image on the uncorrected volume image.

The device and the method can be used both for the correction of x-ray scattering and also for the correction of beam hardening. For the correction of the two interference effects it is possible to create a separate correction volume image which is able to be overlaid with the uncorrected volume image.

BRIEF DESCRIPTION OF THE DRAWINGS

Further details of the invention can be found in the description below, in which exemplary embodiments of the invention are explained in detail with reference to the enclosed drawing. The figures show.

DETAILED DESCRIPTION OF THE INVENTION

Figure 1:
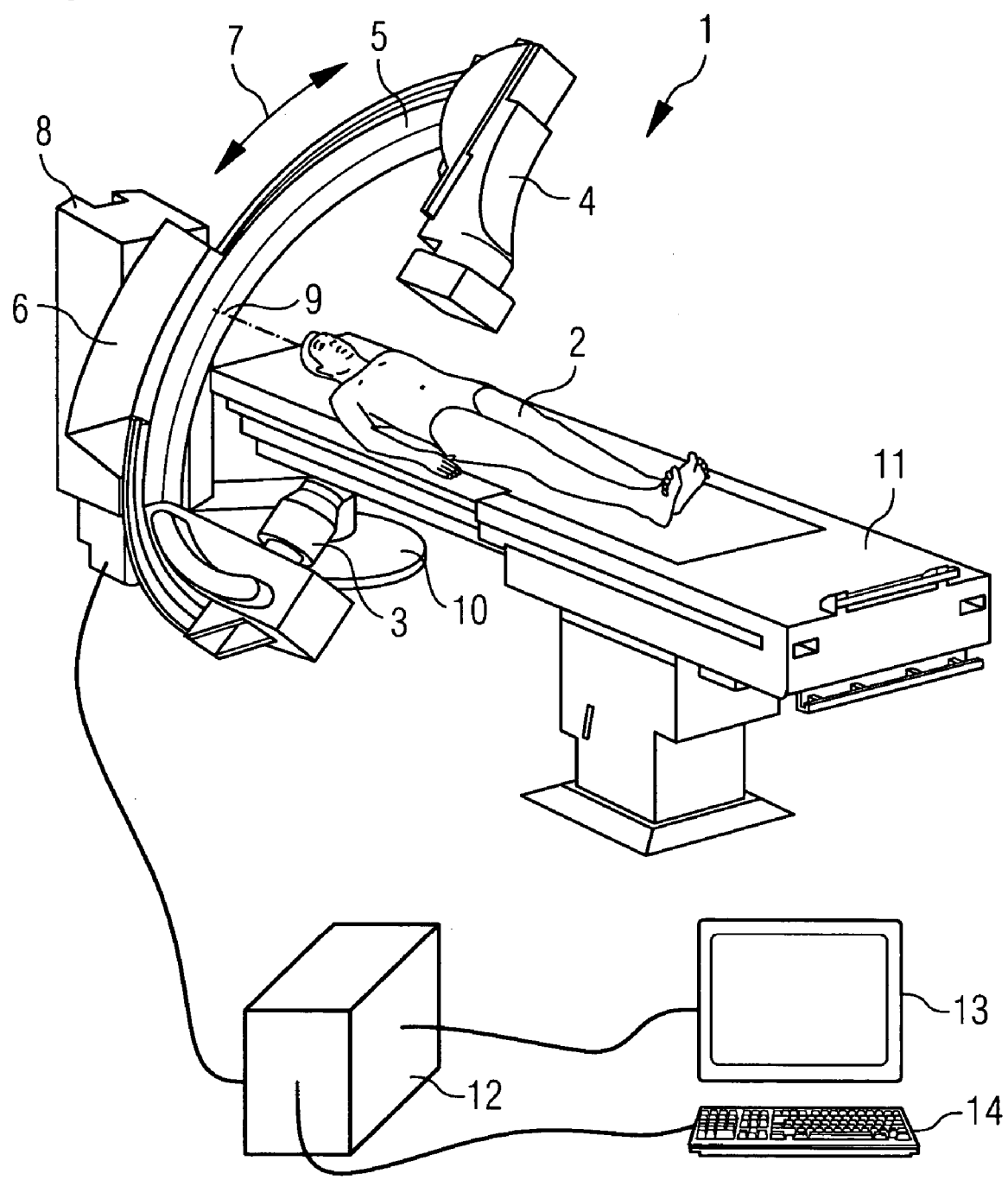
FIG. 1 a perspective view of an x-ray system for rotation angiography.

FIG. 1 shows the perspective view of an x-ray system 1 which can be used for rotation angiography. The x-ray system 1 allows computer tomographic volume reconstruction of the internal structure of a patient 2. The x-ray system 1 comprises an x-ray tube 3 and a detector 4 which records the x-radiation emitted by the x-ray tube 3. On its way to the detector 4 the x-radiation passes through the patient 2 so that the detector 4 records projection images of the patient 2.

The x-ray tube 3 and the detector 4 are attached to a C-arm 5 which is held by a holder 6. The C-arm 5 is supported in the holder 6 so that it can be moved in a circular direction 7. The holder 6 for its part is accommodated on a stand 8 rotatable around an axis of rotation 9. The stand 8 is accommodated on a floor mounting 10 which allows the stand 8 to be moved.

During operation of the x-ray system 1 the C-arm 5 executes a rotation around the axis of rotation 9 and, in doing so, moves around the patient bed 11 on which the patient 2 is supported.

The detector 4 is connected to an evaluation unit 12 which calculates from the projection image a volume representation of the internal structure of the patient 2. The volume image can for example be shown on a monitor 13. Units such as input units 14 are connected to the evaluation unit 12 with which the x-ray system 1 is controlled.

In this connection it should be pointed out that the volume image is three-dimensional data records pertaining to the structure of the patient 2. The volume image can also be displayed in two dimensions on the monitor 13 by for example calculating a cross-sectional image through the volume image and displaying it on the monitor 13.

Various reconstruction algorithms for the reconstruction of the volume images are available to the person skilled in the art: For example the filtered back-projection for two-dimensional parallel or sectoral geometry and specific algorithms for spiral computer tomography.

In particular the person skilled in the art is familiar with the approximative Feldkamp algorithm from FELDKAMP, L. A., DAVIS, L. C., KRESS, J. W.: Practical cone-beam algorithm. J. Opt. Soc. Amer. A, belt 6, 1984, S. 612-619 as well as generalizations from WIESENT, K. [u. a.]: Enhanced 3-D Reconstruction Algorithm for C-arm Systems Suitable for Interventional Procedures. IEEE TRANS. MED. IMAGING, Vol. 19, No. 5, May 2000, P. 391-403, furthermore exact reconstruction algorithms for three-dimensional cone beam computer tomography from KATSEVICH, A: Analysis of an exact algorithm for spiral cone beam CT. Phys. Med. Biol., Vol. 47, 2002, P. 2583-2597.

A significant property of the known reconstruction algorithms is their linearity. Because of the linearity of the reconstruction procedure the reconstruction of a correction volume image can be separated from the reconstruction on the basis of the uncorrected projection images:

$$B(f_0+\delta f)=B(f_0)+B(\delta f)=B_0+\delta B \tag{\#1}$$

In this case $f_0$ designates an uncorrected projection data record, $\delta f$ a correction to the projection data record and B designates the volume image reconstruction, for example with one of the known methods. $B_0$, $\delta B$ designate reconstructed volume images.

A projection data record $f_0$ consists of the series of projection images and of the projection directions acquired for a rotation of the C-arm 5. The following then applies for the protection data record: $f_0$:$f_0=f_0(u,v,w)$, with the row and column variables u,v on the detector and the projection angle variable w, which includes an area >180 degrees. The same indexing applies for the correction data.

The method described here is based on the presence of two volume images: an uncorrected volume image $B_0$ and a correction volume image $\delta B$ as well as the option of explicitly overlaying the two images. This achieves a flexibility which makes it possible for the user to control the degree and the type of admixture of the correction image themselves and to incorporate their empirical knowledge.

In this case different variations are possible.

The simplest correction is that of global linear admixture:

$$B_c=B_0+c\cdot\delta B \tag{\#2}$$

with the correction volume image $\delta B$ is multiplied by a weighting factor c>0 and then linearly superimposed.

With c=1 the standard correction in accordance with equation (#1) is produced. With c<1 the correction and can be attenuated, for example if the standard correction tends towards overcompensation. With c>1 the correction effect can finally be enhanced if the standard correction turns out to be too weak.

A generalization is that of global additive non-linear admixture $$B_\alpha=B_0+\alpha(\delta B) \tag{\#3}$$

in equation (#3) $\alpha$ means a generally non-linear characteristic curve of the gray value area of the correction volume image. $\alpha$ operates in this case pixel-by-pixel or voxel-by-voxel on the gray values of the correction image.

For example for a characteristic curve with exponential gradation, the following relationship applies:

a and b are entered for the smallest and the largest gray value in the correction image $\delta B$ and A=b−a for the extent of the gray value range. The correction is to be spread over the gray value range A'=cA, for c>1, or compressed, for c<1. Then, for any given gray value y between a and b:

$$\alpha(y)=\text{appr}+c(2/A)^{\beta-1}(y-a)^\beta \text{ for } a \leq y \leq (a+b)/2 \quad (\#4a)$$

$$\text{and } \alpha(y)=\text{appr}+cb-\alpha(a+b-y) \text{ for } (a+b)/2 \leq y \leq b \quad (\#4b)$$

for $\beta=1$ the equations (#4a-b) change into the equations (#1) for linear admixture.

Figure 2:
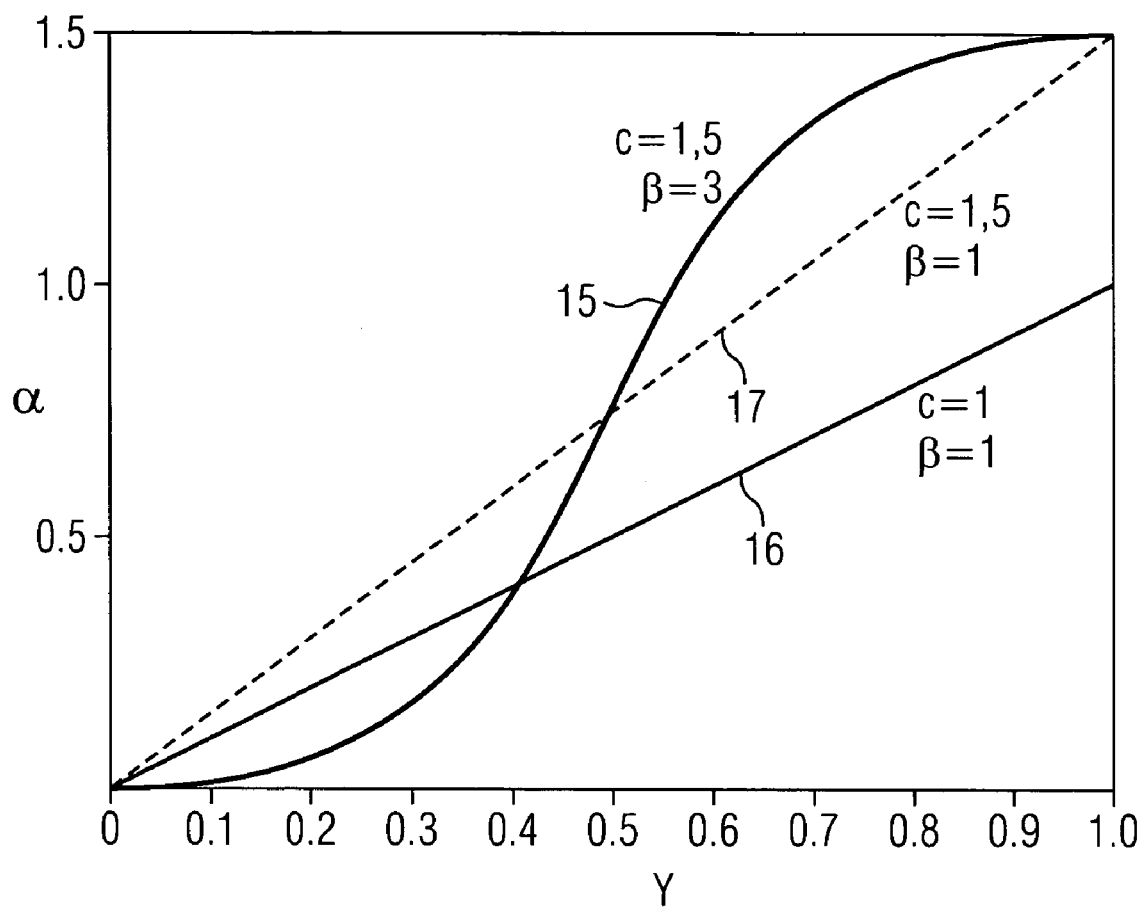
FIG. 2 a diagram with different weighting functions.

The diagram in FIG. 2 illustrates the example of a characteristic curve 15 with $\beta=3$, c=1.5, a=0, b=1. The further linear characteristic curves 16 and 17 each illustrate the case $\beta=1$ and c=1.5 as well as $\beta=1$ and c=1.

It should be pointed out that in equation (#3) any suitable monotonous characteristic curve can of course be used, including the known technique of histogram equalization for example.

A further option is that of local admixture. Local admixture is applicable to both the stated forms of execution, linear or also non-linear admixture. With local admixture, instead of the default global admixture extending over the entire image volume, the uncorrected image volume is only modified linearly or non-linearly in a spatial area of interest to be selected by the user. In order however to prevent discontinuities at the edges of the area of interest, the correction must be multiplied by a spatial window function which preferably has the value 1 within the area of interest and at the edge of the area of interest falls smoothly to the value 0.

Various options are described below with reference to FIGS. 3 and 4 for creating a correction of volume image and overlaying it with the volume image.

Figure 3:
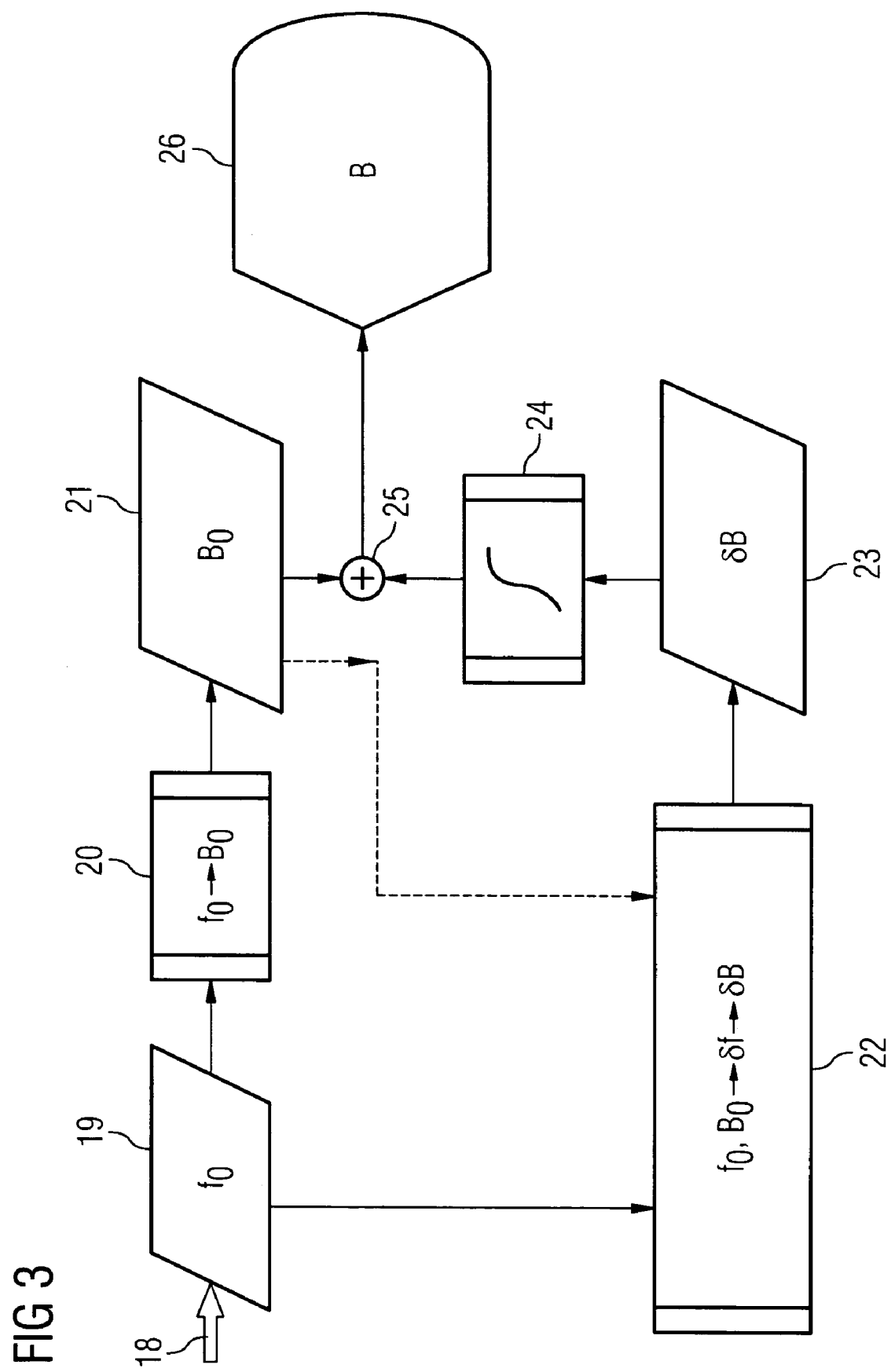
FIG. 3 a block diagram which shows the execution sequence of a correction procedure.

In accordance with FIG. 3 a data acquisition 18 delivers projection image data 19 from which an uncorrected volume image 21 is created by a reconstruction 20. On the basis of the uncorrected projection image data 19 and the uncorrected volume image 21 an error correction 22 is undertaken and a correction volume image 23 created. The error correction 22 can be executed for example by undertaking a re-projection on the basis of the uncorrected volume image 21 and comparing the re-projected projection images created in this way with the original projection at image data 19.

The correction volume image 23 is subjected to a weighting 24. By a subsequent addition 25 of the uncorrected volume image 21 and the correction image 23, the corrected volume image 26 is finally created.

One advantage of the separate reconstruction of the correction volume image 23 is that the processing effort for the reconstruction of the correction volume image 23 can be reduced by moving to a coarser spatial resolution. Since the image artifacts to be corrected are as a rule formed over large areas, this does not significantly worsen the image quality of the corrected volume image 23.

Figure 4:
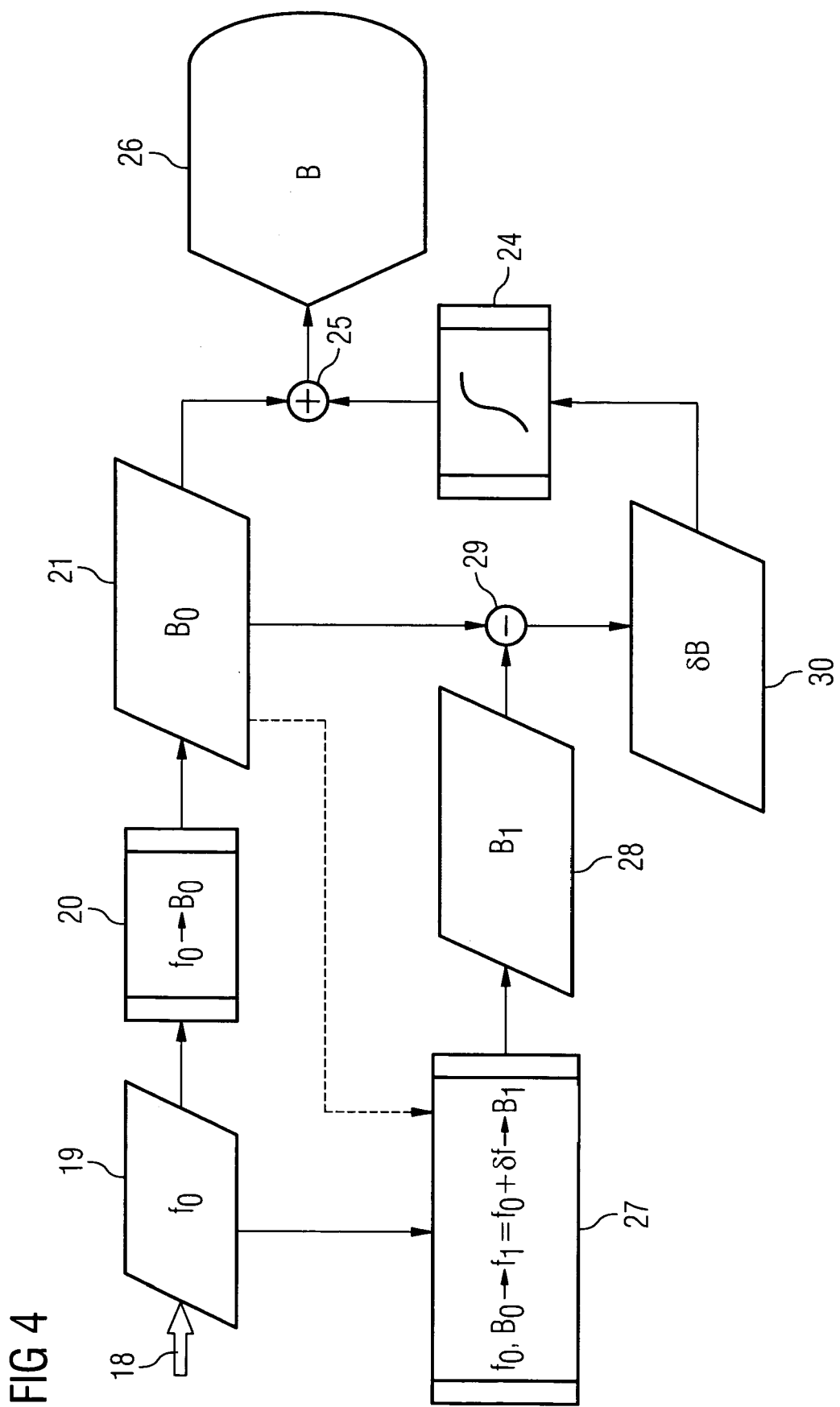
FIG. 4 a block diagram with a further embodiment of the correction procedure.

In addition it is also possible, as shown in FIG. 4 to create corrected projection image data in an error correction 27, and from the corrected projection image data to reconstruct a provisional corrected volume image 28. Through a subsequent subtraction 29 a difference image 30 is formed between the uncorrected volume image 21 and the provisionally corrected volume image 28. The difference image 30 is then subjected to a weighting 24 and after an addition 25 of the uncorrected volume image with the weighted difference image 30 the corrected volume image 26 is finally produced.

It should be pointed out that for the exemplary embodiments described with reference to FIGS. 3 and 4 post-reconstructive correction procedures are employed in each case. It is however also possible to create a correction image with the aid of a pre-constructive correction procedure. In this case the correction image is constructed on the basis of the projection images. This is for example of the case for what is known as a water correction for correcting beam hardening. Since pre-constructive correction processes cannot as a rule completely eliminate the errors, the option of being able to overlay a correction image weighted with an uncorrected volume image, especially in conjunction with pre-constructive correction procedures, is of advantage.

The separate reconstruction or a correction volume image is associated with the following advantages:

The presence of a separate correction volume image produces a greater flexibility since with the superimposition onto the—uncorrected or only pre-corrected—volume image, the weighting of the correction in the gray value scale, spatially restricted if necessary, can be adapted.

The control of the adjustment by the user is furthermore as a rule significantly faster to adapt then a new overall reconstruction with changed correction parameters.

The invention claimed is:

1. A computer tomography medical examination device, comprising:
   a radiographic source for illuminating an object being medically examined from different projection angles;
   a detector for detecting a radiation from the radiographic source and recording a projection image of the object; and
   an evaluation unit connected downstream from the detector for reconstructing a volume image of the object from the projection image and correcting an image error caused by interference effects in the volume image,
   wherein an uncorrected volume image and a correction volume image are created by the evaluation unit,
   wherein a corrected volume image is created by the evaluation unit by superimposing the correction volume image on the uncorrected volume image with an user selected weighting function,
   wherein the evaluation unit creates the uncorrected volume image from the projection image,
   wherein the uncorrected volume image is re-projected to create a corrected projection image,
   wherein the correction volume image is created from the corrected projection image.

2. The device as claimed in claim 1, wherein the uncorrected volume image and the correction volume image are combined linearly.

3. The device as claimed in claim 1, wherein the uncorrected volume image and the correction volume image are combined non-linearly using a weighting function with an image value of the correction volume image as an argument.

4. The device as claimed in claim 1, wherein a weighting with a locally-restricted window function is executed on the correction volume image.

5. The device as claimed in claim 1, wherein the correction volume image corrects an x-ray scattering of the volume image.

6. The device as claimed in claim 1, wherein the correction volume image corrects a beam hardening of the volume image.

7. The device as claimed in claim 1, wherein the object is a live animal or human patient.

8. A method for correcting an image error in a volume image caused by interference effects, the volume image reconstructed from a projection image of an object being medically examined, comprising:
   illuminating the object from different projection angles with a radiographic source;

recording a projection image of the object from the radiographic source;

creating an uncorrected volume image and a correction volume image from the projection image; and generating a corrected volume image by superimposing the correction volume image on the uncorrected volume image with an user selected weighting function, wherein the uncorrected volume image is created from the projection image, wherein the uncorrected volume image is re-projected to create a corrected projection image, wherein the correction volume image is created from the corrected projection image.

9. The method as claimed in claim 8, wherein the uncorrected volume image and the correction volume image are combined linearly.

10. The method as claimed in claim 8, wherein the uncorrected volume image and the correction volume image are combined non-linearly by weighting the correction volume image with a non-liner weighting function.

11. The method as claimed in claim 8, wherein the correction volume image is weighted with a spatially-restricted window function.

12. The method as claimed in claim 8, wherein an x-ray scattering of the volume image is corrected.

13. The method as claimed in claim 8, wherein a beam hardening of the volume image is corrected.

14. The method as claimed in claim 8, wherein the object is a live animal or human patient.

* * * * *